US00PP08620P

United States Patent [19]

Carmel

[11] Patent Number: Plant 8,620

[45] Date of Patent: Mar. 1, 1994

[54] ROSE PLANT: ODEM

[75] Inventor: Carmi Carmel, Moshav Ha'yogev, Israel

[73] Assignee: Yoval Agriculture Products, Ltd., Moshav Ha'yogev, Israel

[21] Appl. No.: 783,931

[22] Filed: Oct. 29, 1991

[30] Foreign Application Priority Data

Oct. 30, 1990 [IL] Israel ..... 1625/90

[51] Int. Cl.[5] ..... A01H 5/00

[52] U.S. Cl. ..... Plt./20

[58] Field of Search ..... Plt. 20

[56] References Cited

PUBLICATIONS

Harings P.A. (Ed.) "Mme. Georges Delbard" *Modern Roses* 9 American Rose Society, Shreveport, La., 1986, p. 181.

*Primary Examiner*—James R. Feyrer

*Attorney, Agent, or Firm*—Pollock, Vande Sande & Priddy

[57] ABSTRACT

A rose plant exhibiting good resistance to powdery mildew and being characterized by non-fragrant flowers, prolific growth and flower production, good self-rooting and a large number of water shoots.

2 Drawing Sheets

CROSS REFERENCE TO RELATED APPLICATIONS

This application is related to the plant Carola, U.S. patent application Ser. No. 07/767,546, filed Sept. 27, 1991, a continuation of U.S. patent application Ser. No. 07/387,837, filed Aug. 1, 1989, now abandoned.

FIELD OF THE INVENTION

The present invention is concerned with a new variety of a Hybrid Tea rose discovered by me and being a mutation of Carola, U.S. patent application Ser. No. 07/767,546, which is a mutation of Deladel (Mme. G. Delbard), U.S. Plant Pat. No. 4,391, issued Mar. 6, 1979.

BACKGROUND OF THE INVENTION

This mutation was discovered as a branch on a Carola plant in 1990 on a cultivated area in a farm, located in Moshav Ha'yogev, located in Israel Valley, Israel, with an average night temperature of 25° C. in summer and 0°-5° C. in winter, and day temperatures of 30° C. in summer and 15° C. in winter.

The branch was vegetatively propagated from cuttings by self-rooting. From these cuttings plants were grown in a greenhouse where they were further vegetatively propagated by self-rooting.

The resulting plants were found to be stable in their botanical characteristics, as are described below and as illustrated by typical plants parts in the attached photographs.

Asexual propagative of this new variety of performed at Moshav Ha'yogev, Israel.

The observations were made between the present invention, the parent plant, Carola, and the grandparent plant, Deladel.

| | Odem | Carola | Deladel |
|---|---|---|---|
| Average number of petals | 39–48 | 33–40 | 18–25 |
| Size of Petal | | | |
| length | 37–45 mm | 50–55 mm | does not differ from Carola |
| width | 39–49 mm | 55–60 mm | does not differ from Carola |

-continued

| | Odem | Carola | Deladel |
|---|---|---|---|
| Flower | | | |
| diameter | ca. 80 mm | ca. 110 mm | does not differ from Carola |
| color of upper side | RHS[1] 46 AB | RHS 53 A | RHS 53 A |
| color of lower side | RHS 52 A | RHS 53 C | RHS 53 B |
| Petal's reflex | medium | strong | strong |
| Size of spot at base of inner side of petal | small | medium | very small |
| Color of spot at base of inner side of petal | yellow | white | yellow |
| Fragrance of flower | none | none | slight, not sweet or spicy |
| Average number of cut-flowers per plant per month (year-round production) | 2.5 | 1.85–2.00 | 0.90–1.25 |
| Average number of water shoots in first year after planting | 4–6 | 4–6 | 2–3 |
| Plant height in 6 months after planting | 90–130 cm | 170–180 cm | 80–90 cm |
| Time from planting to commercial flower production | 5–6 months | 6–8 months | 10–12 months |
| Length of flowering stem | 40–60 cm | 70–80 cm | 70–90 cm |
| Relative thickness of flowering stem | thin | medium | thick |
| Number of flowering stems per plant per year | about double as for Carola | | |
| Leaf measurements[2] | | | |
| upper leaf | 5.5 cm | 7.5 cm | unknown |
| leaflets at upper part | 4.6 cm | 6.0 cm | unknown |
| leaflets at center part | 4.0 cm | 5.4 cm | unknown |
| leaflets at bottom part | 3.0 cm | 4.1 cm | unknown |

-continued

| | Odem | Carola | Deladel |
|---|---|---|---|
| Vase life | 15–18 days | 12–15 days | unknown |

[1]Royal Horticultural Society of London, England (RHS) Colour Chart
[2]Based upon the average sizes of twenty leaves of each variety sampled from plants grown side-by-side under the same roof and conditions in a greenhouse in Moshav Ha'yogev, Israel.

SUMMARY OF THE INVENTION

The present invention provides a hybrid tea rose variety which include the following characteristics which distinguish the new variety from cultivars to which it is related:

Distinctly smaller flowers in comparison with Carola and Deladel and

Distinctly different color of basal spot of petal in comparison with Carola.

BRIEF DESCRIPTION OF THE DRAWINGS

FIG. 1 represents a typical specimen of the present invention, illustrating a leaf, a flower bud, a flower bud at picking stage, a part of the stem, leaflets, and flowers at various opening stages.

FIG. 2 represents a side-by-side comparison of flower size, bud size, color and size of petal, color and size of basal spot between a typical specimen of the present invention, Odem, and the parent variety, Carola.

The colors in the drawings are as true as is reasonably possible in an illustration depicting green and red colors. The photographs were taken from comparable specimens, grown under exactly the same conditions, in a greenhouse at Moshav Ha'yogev, each on its own roots, and being visibly healthy.

BOTANICAL DESCRIPTION

Based on observations made in Moshav Ha'yogev, Israel, in 1990 and 1991 in a greenhouse.

| | |
|---|---|
| Plant | |
| growth habit | semi-upright |
| Young shoot | |
| anthocyanin coloration | medium to strong |
| hue of anthocyanin coloration | red-brown |
| Prickles | present |
| Prickle | |
| shape of upper side | concave to straight |
| shape of lower side | concave |
| Short Prickles | |
| number | few |
| Long Prickles | |
| number | medium |
| Leaf | |
| length | 120–150 mm |
| width | 75–115 mm |
| green color | medium |
| glossiness of upper side | weak |
| Leaflet | |
| cross section | straight |
| undulation of margin | weak to medium |
| Terminal Leaflet | |
| length of blade | 50–65 mm |
| maximum width | 30–43 mm |
| length of petiole | 15–20 mm |

-continued

| | |
|---|---|
| shape of base | rounded |
| Flowering Shoot | |
| number of flowers | few |
| Flowering habit | continuous |
| Flowering Pedicel | |
| number of hairs or prickles | very few to few |
| Flower Bud | |
| longitudinal section | ovoid |
| Flower | |
| type | double |
| number of petals | 40–53 |
| diameter | ca. 80 mm |
| view from above | rounded |
| side view of upper part | flattened-convex |
| side view of lower part | flat |
| fragrance | none |
| Sepal | |
| length | 30–43 mm |
| extension | medium |
| Petal | |
| size | |
| length | 37–45 mm |
| width | 39–49 mm |
| shape | rounded |
| color of middle zone of inner side | RHS 46 AB dark red Currant red |
| color of marginal zone of inner side | RHS 46 AB dark red Currant red |
| basal spot on inner side | present |
| size of basal spot on inner side | small |
| color of basal spot on inner side | RHS 3 B yellow |
| color of middle zone of outer side | RHS 52 A Deep red Crimson |
| color of marginal zone of outer side | RHS 52 A Deep red Crimson |
| basal spot on inner side | present |
| size of basal spot on outer side | small |
| color of basal spot on outer side | RHS 3 C yellow |
| reflex of margin | medium |
| undulation of margin | very weak to weak |
| Stamen | |
| predominant color of filament | orange-red |
| Style | |
| length | long |
| predominant color | purple |
| hairiness of upper half | absent |
| Stigma | |
| position as compared with anthers | same level |
| Seed Vessel | |
| size | small |
| shape of longitudinal section | funnel-shaped |
| Time of Beginning of Flowering | medium |
| Resistance to Powdery Mildew | good |
| Self-rooting | good |

I claim:

1. A new and distinct variety of a rose plant of a Hybrid Tea rose variety, named Odem, as shown and described, and consisting mainly of plants being vigorous growing, showing a smaller flower than Carola, containing a large number of petals, having non-fragrant flowers, with petals' color dark red/current red/RHS 46 AB, with a small-sized yellow spot at their base, with early and prolific flower production, and having fast and good propagating features.

* * * * *

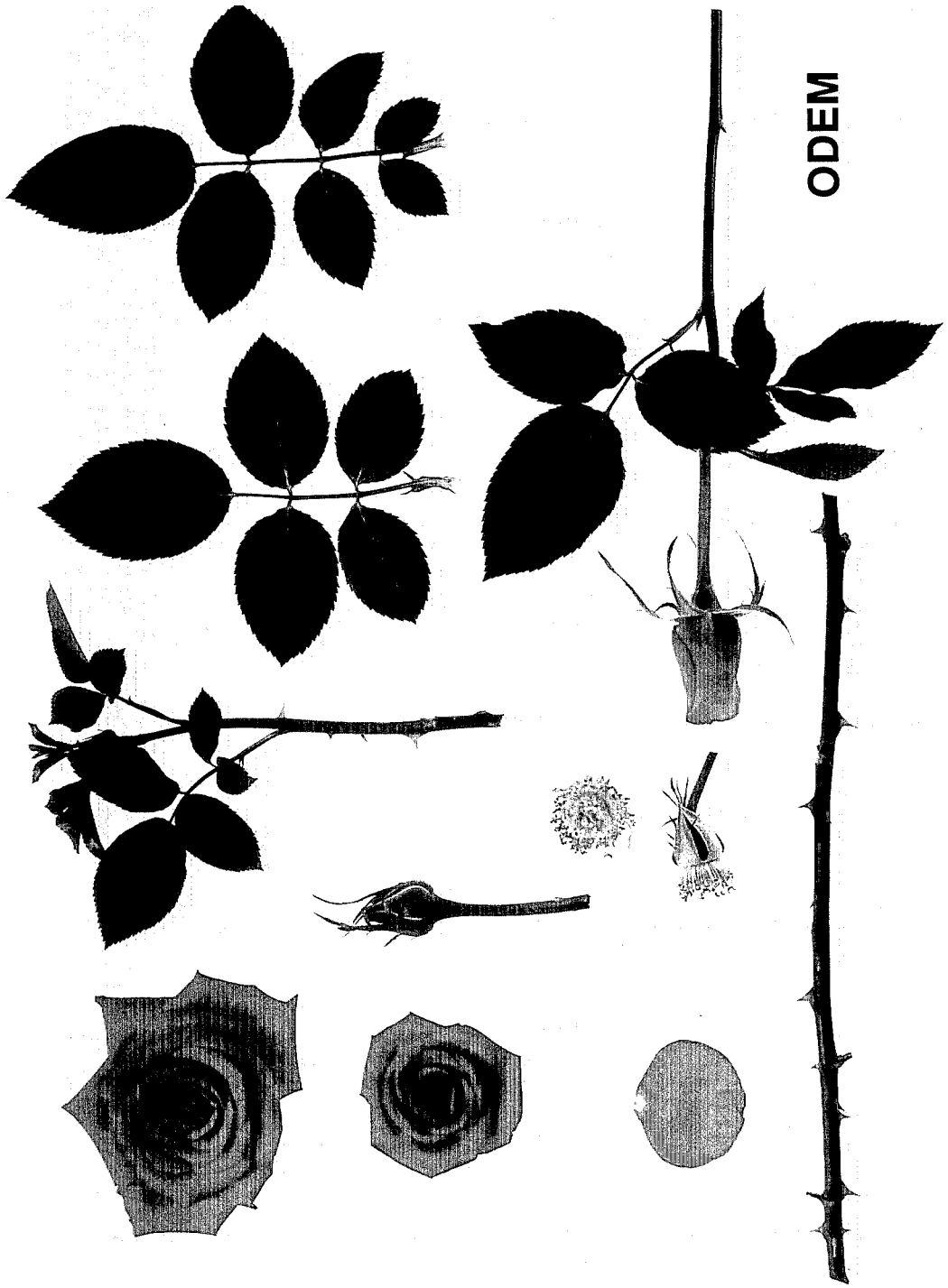
ODEM

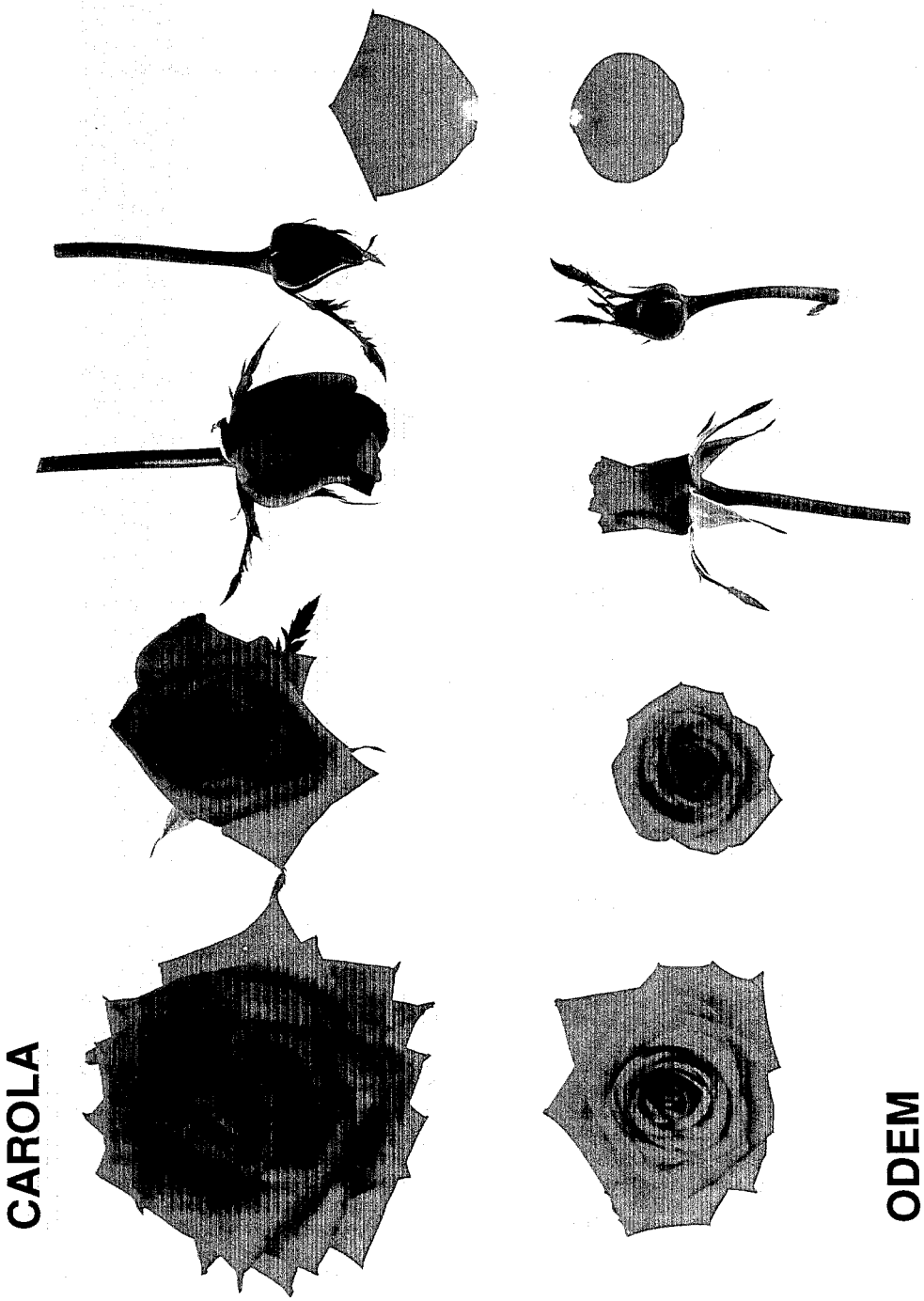
CAROLA
ODEM